United States Patent
Roffler et al.

[11] Patent Number: 6,043,367
[45] Date of Patent: Mar. 28, 2000

[54] PROACTIVE ANTITUMOR COMPOUNDS

[76] Inventors: Steve Roffler, Yen Geo Yuan Rd., Section 2, Lane 61, Alley 4, No. 14, 3F; Ji-Wang Chern, Hsin-Hai Road, Section 4, Lane 77, No. 108, 9F, both of Taipei; Ye-Lin Leu, Jie-Shou Road, Section 3, Lane 983, No. 5, Tao Yuan, all of Taiwan

[21] Appl. No.: 09/164,058

[22] Filed: Sep. 30, 1998

[51] Int. Cl.$^7$ .................................................. C07D 491/22
[52] U.S. Cl. .................................................................. 546/48
[58] Field of Search .................................................... 546/48

[56] References Cited

U.S. PATENT DOCUMENTS

| | | | |
|---|---|---|---|
| 4,604,463 | 8/1986 | Miyasaka et al. | 544/125 |
| 4,975,278 | 12/1990 | Senter et al. | 424/94.3 |
| 4,981,968 | 1/1991 | Wall et al. | 544/361 |
| 5,559,235 | 9/1996 | Luzzio et al. | 544/361 |
| 5,561,119 | 10/1996 | Jacquesy et al. | 514/34 |
| 5,602,141 | 2/1997 | Bedeschi et al. | 514/279 |
| 5,621,002 | 4/1997 | Bosslet et al. | 514/451 |
| 5,632,990 | 5/1997 | Bagshawe et al. | 424/178.1 |
| 5,658,568 | 8/1997 | Bagshawe | 424/134.1 |
| 5,677,286 | 10/1997 | Shull et al. | 514/25 |
| 5,710,135 | 1/1998 | Leenders et al. | 514/34 |
| 5,726,181 | 3/1998 | Hausheet et al. | 514/283 |
| 5,734,056 | 3/1998 | Burk et al. | 546/48 |
| 5,760,072 | 6/1998 | de Bont et al. | 514/449 |

OTHER PUBLICATIONS

Azoulay et al., "Prodrugs of anthracycline antibiotics suited for tumor–specific activation", Anti–Cancer Drug Design (1995), 10:441–450.

Chen et al., "Cure of Malignant Ascites and Generation of Protective Immunity by Monoclonal Antibody–Targeted Activation . . . Prodrug in Rats", Int. J. Cancer, (1997), 73:392–402.

Cheng et al., Poly(ethylene glycol) Modification of β–glucuronidase–antibody conjugates for solid–tumor Therapy by Targeted Activation of Glucuronide Prodrug, Cancer Immunol. Immunother. 44:305–315 (1997).

Haisma et al., "Comparison of Two Anthracycline–Based Prodrugs for Activation by a Monoclonal . . . Treatment of Cancer", Cell Biophysics, (1994) 24/25:185–192.

Haisma et al., "A monoclonal antibody–β–glucuronidase conjugate as activator of the prodrug epirubicin–glucuronide . . . treatment of cancer", British Journal of Cancer, 66(3): pp. 474, Sep. 1, 1992.

Leenders et al., "β–Glucuronyl Carbamate Based Pro–moieties Designed for Prodrugs in ADEPTacology" Tetrahedron Letters, 36:10 pp. 1701–1704, 1995.

Leenders et al., "Synthesis and Evaluation of Novel Daunomycin–Phosphate–Sulfate–β–Glucuronide and β–Glucoside Prodrugs for Application in ADEPT" Bioorganic & Medicinal Chemistry Letters, 5:24 2975–80, 1995.

Murdter et al., "Enhanced Uptake of Doxorubicin into Bronchial Carcinoma: β–Glucuronidase Mediates Release of Doxorubicin from a Glucuronide Prodrug (HMR 1826) at the Tumor Site" Cancer Research 57:2440–2445, 1997.

Schmidt et al., "Glucuronide Prodrugs of Hydroxy Compounds for Antibody Directed Enzyme Prodrug Therapy (ADEPT): A Phenol Nitrogen Mustard Carbamate" Bioorganic & Medicinal Chemistry Letters, 7:8 1071–76, 1997.

Wang et al., "Specific Activation of Glucuronide Prodrugs by Antibody–targeted Enzyme Conjugates for Cancer Therapy" Cancer Research 52, 4484–4491, 1992.

Roffler et al., "Anti–neoplastic glucuronide prodrug treatment of human tumor cells targeted with a clonal antibody––enzyme conjugate" Biochemical Pharmacology, 42:10 pp. 2062–2065, 1991.

Roffler et al., "A Quick method for Detecting Metabolic Cooperation", Biochemical Pharmacology, 42(10): 2061–2062, 1991.

*Primary Examiner*—Patricia L. Morris
*Attorney, Agent, or Firm*—Fish & Richardson P.C.

[57] ABSTRACT

The present invention features proactive antitumor compounds of the following formula:

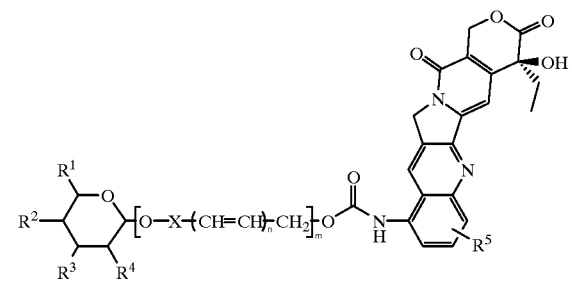

wherein $R^1$ is COOZ; Z being H, alkali metal, alkaline earth metal, an ammonium group which is optionally substituted with one or more alkyl groups, or a carboxyl protecting group; each of $R^2$, $R^3$, and $R^4$, independently, is OH or $OR^a$; $R^a$ being a hydroxyl protecting group; X is benzene or pyridine, optionally substituted with $R^b$; $R^b$ being H, $C_{1-5}$ alkyl, $C_{1-5}$ alkoxy, $NO_2$, F, Cl, Br, $SO_3H$, and CN; $R^5$ is H or OH; and each of n and m, independently, is 0 or 1; or a salt thereof.

19 Claims, No Drawings

PROACTIVE ANTITUMOR COMPOUNDS

BACKGROUND OF THE INVENTION

Cancer is the second leading cause of death in the United States. Estimated by the American Cancer Society, approximately 1.2 million new cancer cases will be diagnosted and more than half a million Americans are expected to die from cancer this year. The types of cancer treatments usually include immunotherapy, surgery, radiation, hormones, and chemotherapy.

Chemotherapy, despite being a powerful cancer treatment, especially for inoperable or metastatic forms, does suffer from a few problems. The most prominent problem is the low specificity of the anticancer agents. That is, most anticancer agents do not distinguish normal cells from cancer cells to an appreciable level. Many anticancer agents are also not very hydrophilic, thus creating solubility problem in serum.

SUMMARY OF THE INVENTION

This invention relates to a proactive antitumor compound or a salt thereof. A proactive antitumor compound is meant a relatively non-cytotoxic compound, which upon activation, is converted into a cytotoxic compound. The proactive antitumor compound of this invention is of the following formula:

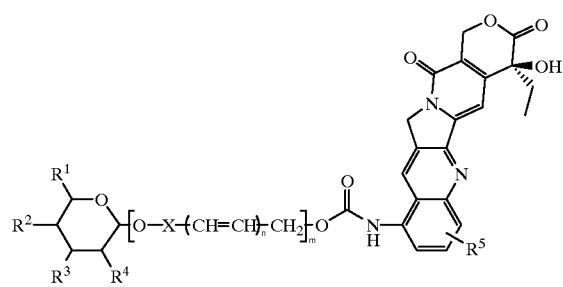

$R^1$ represents COOZ, wherein Z is H, alkali metal, alkaline earth metal, ammonium, an organic ammonium group, or a carboxyl protecting group. Each of $R^2$, $R^3$, and $R^4$, independently, is OH or $OR^a$, in which $R^a$ is a hydroxyl protecting group. X is benzene or pyridine, optionally substituted with $R^b$, which can be H, $C_{1-5}$ alkyl, $C_{1-5}$ alkoxy, $NO_2$, F, Cl, Br, $SO_3H$, or CN. $R^5$ is H or OH. Each of n and m, independently, is 0 or 1.

A salt of a compound covered by the above formula is within the scope of this invention. A salt is formed when Z is an alkali metal ion, e.g., a sodium ion or a potassium ion; an alkaline earth metal ion, e.g., a magnesium ion or a calcium ion; an ammonium ion ($NH_4^+$); or an organic ammonium group such as tetramethylammonium ion or diisopropylethylammonium ion. As another example, if an amino group is present on the benzene or pyridine ring X, it can form a salt with a negatively charged counterion. Suitable counterions include, but are not limited to, chloride, hydrochloride, bromide, iodide, sulfate, nitrate, phosphate, or acetate.

A $C_{1-5}$ alkyl means a straight or branched hydrocarbon chain containing 1 to 5 carbon atoms. Examples of alkyl include, but are not limited to, methyl, ethyl, propyl, isopropyl, butyl, isobutyl, sec-butyl, tert-butyl groups. By "$C_{1-5}$ alkoxy" is meant —O—$C_{1-5}$ alkyl.

A carboxyl protecting group can be, e.g., a methyl ester, a methoxymethyl ester, a trimethylsilyl ester, or a dimethylamide. Some typical examples of a hydroxyl protecting group include methoxymethyl ester, tetrahydropyranyl ether, trimethylsilyl ether, and acetate ester. More carboxyl or hydroxyl protecting groups are described in "Protective Groups in Organic Synthesis" by T. W. Greene, John Wiley & Sons, Inc. (1981).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications mentioned herein are incorporated by reference in their entirety. In case of conflict, the present specification, including definitions, will control. In addition, the materials, methods, and examples are illustrative only and not intended to be limiting.

Other features or advantages of the present invention will be apparent from the following detailed description of several embodiments, and also from the appending claims.

DETAILED DESCRIPTION

The present invention features a proactive antitumor compound of the following formula, which is composed of 3 moieties.

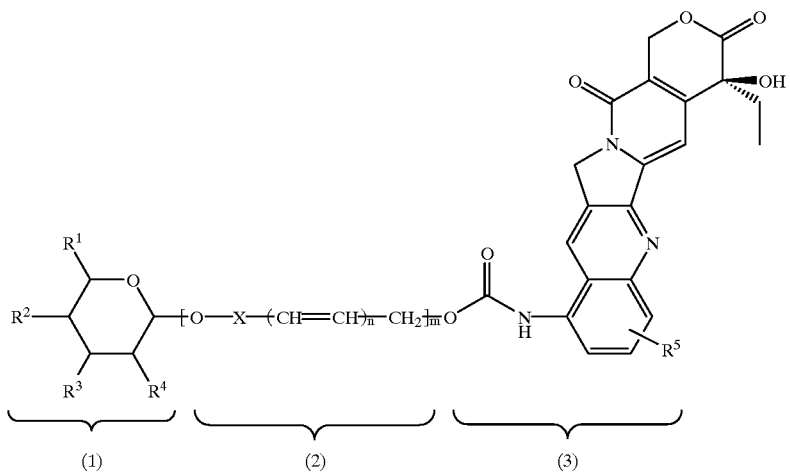

Moiety (1) is a glucuronide or a derivative thereof; moiety (2) is an electron-transporting linker that joins moieties (1) and (3) together; and moiety (3) is a known cytotoxic agent. Moiety (3), when linked to moieties (1) and (2), is more water-soluble and thus is preferred. Further, the proactive antitumor compound of this invention can be preferentially activated and converted into the more cytotoxic moiety (3) at a tumor site with a high concentration of glucuronidase, thereby significantly increasing the specificity of moiety (3) in targeting tumor cells.

The proactive antitumor compound is rapidly activated by glucuronidase which is enriched at the tumor site, either by endogenously or exogenously methods. The activation process begins with the recognition of moiety (1), a glucuronide or a derivative thereof, by glucuronidase. Glucuronidase binds to moiety (1) and cleaves the ether linkage between moieties (1) and (2). Moiety (2) is then left with an anionic oxide after the enzymatic cleavage. Electrons from the oxide can then travel along moiety (2), resulting in the cleavage of the carbamate linkage between moieties (2) and (3), i.e., the release of a free cytotoxic moiety (3) at the tumor site. For more references on the use of enzymes in activation of proactive compounds, see Senter et al., *Proc. Natl. Acad. Sci. U.S.A.* 1988, 85, 4842–4846 and Bagshawe et al., *Br. J. Cancer* 1988, 58, 700–703.

As the cleavage between moieties (2) and (3) is caused by the above-described electron flow, electron-withdrawing or electron-donating substituents on the benzene or pyridine ring of moiety (2), when present, can have an effect on the releasing rate of moiety (3).

The preparation of the proactive compound can be conducted in two stages. In the first stage, moieties (1) and (2) are coupled by the formation of an ether linkage. In the second stage, moiety (3) is joined to the moiety (1)-moiety (2) conjugate via a carbamate linkage.

Many different routes can be employed to link moieties (1) and (2) together via an ether linkage. Two examples are illustrated in the following Schemes 1 and 2.

In Scheme 1, a protected moiety (1), i.e., methyl 1-α-bromo-2,3,4-tri-O-acetyl-β-D-glucuronate, is first brominated by using titanium tetrabromide. The newly formed bromide is then displaced by the hydroxyl group of p-hydroxybenzaldehyde, thus resulting in an ether linkage. Hydrogenation of the aldehyde affords the benzyl alcohol intermediate.

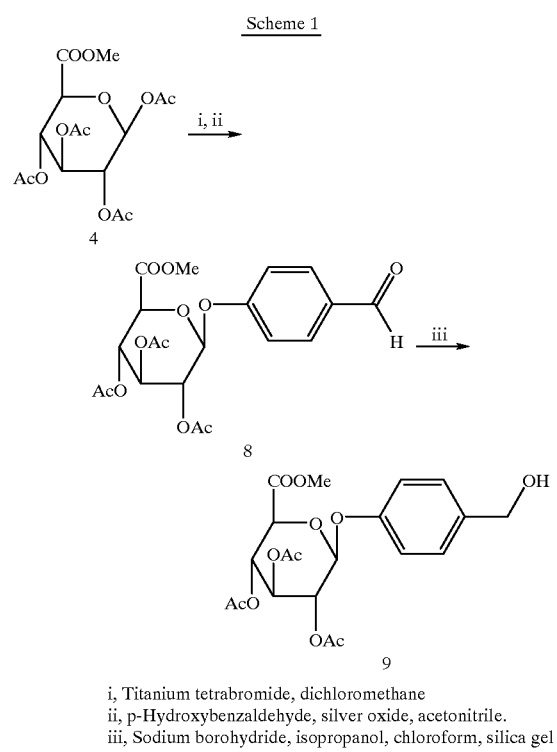

i, Titanium tetrabromide, dichloromethane
ii, p-Hydroxybenzaldehyde, silver oxide, acetonitrile.
iii, Sodium borohydride, isopropanol, chloroform, silica gel Moiety (2) can be lengthened by the presence of a double bond between the benzene ring and the hydroxymethyl group. One way of introducing the double bond is by using 3-(p-hydroxyphenyl)-2-propenal instead of p-hydroxybenzaldehyde.

An alternative route in coupling moieties (1) and (2) is to react the brominated protected moiety (1) with 4-methyl-2nitrophenol in the presence of silver oxide. The 4-methyl group of the benzene ring can be brominated to afford a bromomethane group which can then be converted to benzyl alcohol intermediate. See Scheme 2 below:

Scheme 2

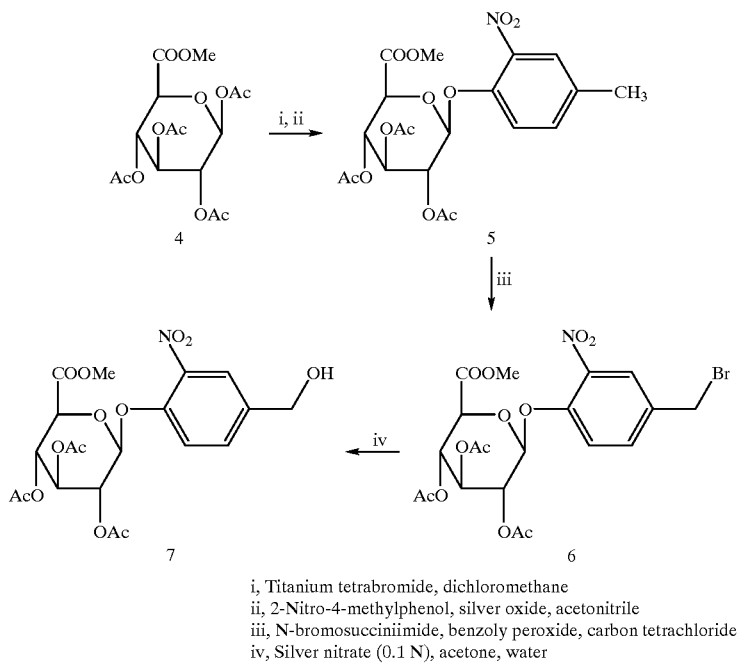

i, Titanium tetrabromide, dichloromethane
ii, 2-Nitro-4-methylphenol, silver oxide, acetonitrile
iii, N-bromosucciniimide, benzoly peroxide, carbon tetrachloride
iv, Silver nitrate (0.1 N), acetone, water After coupling moieties (1) and (2), the acetyl protecting groups of moiety (1) can be removed in basic conditions, e.g., by using sodium methoxide.

One way of forming a carbamate linkage between moiety (2) (i.e., as part of moiety (1)-moiety (2) conjugate) and moiety (3) is by reacting the hydroxyl group of the benzyl alcohol of moiety (2) with an isocyanate group of moiety (3). An isocyanate group can be generated from treating an amino group of moiety (3) with triphosgene. Scheme 3 shows a method of how an amino group of moiety (3) can be formed:

Scheme 3

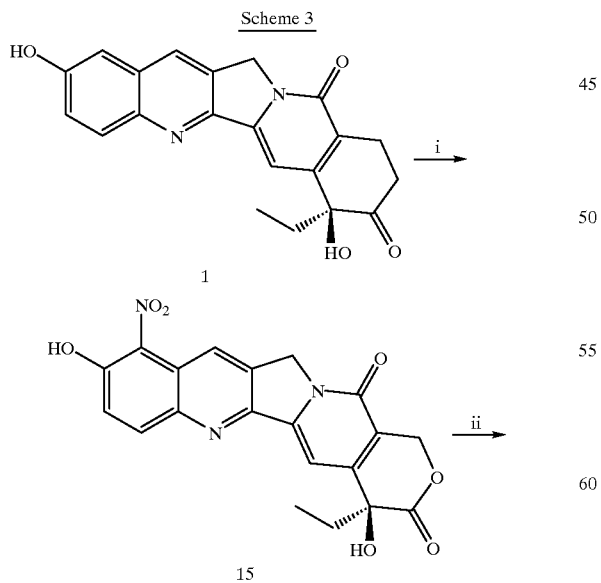

-continued

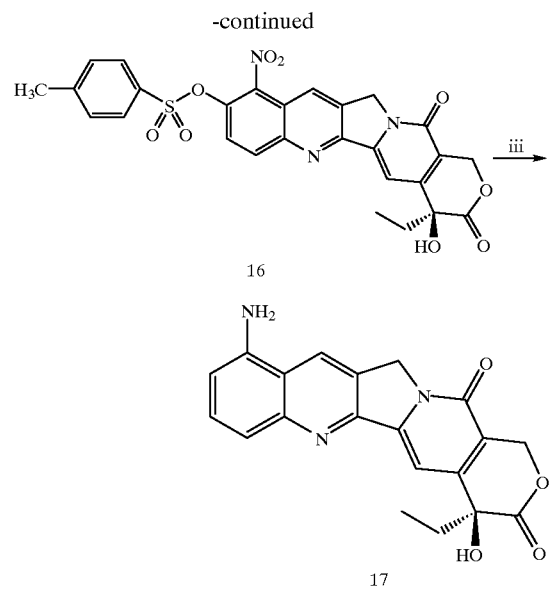

i, Sulfuric acid, nitric acid
ii, Tosyl chloride, triethylamine, DMAP, dichloromethane
iii, Palladium acetate, triphenylphosphine, triethylammonium formate, dioxide The amino group of moiety (3) is then converted into a isocyanate group and subsequently bonded to the hydroxyl group of moiety (2) via a carbamate linkage as detailed in Scheme 4:

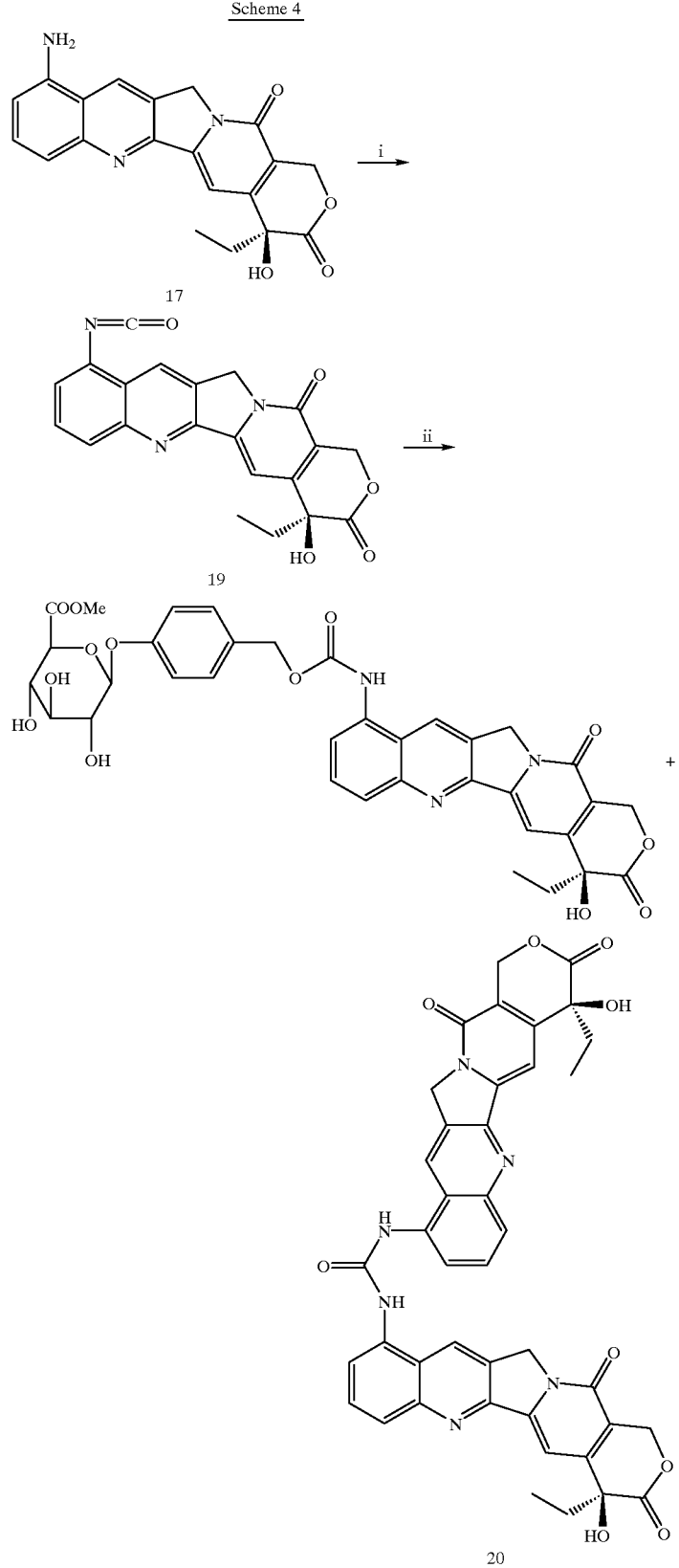
Scheme 4
i, Triphosgene, pyridine
ii, Comp'd 12, pyridine

In the final step, the ester protecting group of moiety (1) can be removed by treating with, e.g., potassium trimethylsilanolate and hydrochloric acid, to afford the proactive compound.

The stability of the proactive compound in serum can be evaluated by using high performance liquid chromatography (HPLC) analysis. For example, the tested compound can be incubated in 95% human plasma at 37° C. in an $CO_2$ atmosphere. Aliquots are taken out from the serum solution after every pre-designed period of time, e.g., every other hour. The proteins present in serum are precipitated, acidified, and dried under reduced pressure. The dried compound is dissolved in the HPLC buffer and then analyzed by HPLC.

The proactive compound can also be tested as to its ability to be cleaved by β-glucuronidase. Specifically, the enzyme and the tested compound are both added to human plasma. Aliquots are then taken out and evaluated in a similar fashion as described above.

Glucuronidase can be selectively enriched at a tumor site by utilizing an antibody-glucuronidase conjugate, in which the antibody targets a specific type of cancerous cell. A fusion protein of an antibody or its fragment can also be employed in place of an antibody. The cancerous cells can be made to express glucuronidase at a high level by introduction of a nucleic acid encoding glucuronidase into these cells. Other sources such as infiltrating lymphocytes or macrophages are also possible sources of glucuronidase in a tumor site.

A pharmaceutical composition of this invention containing a proactive compound of this invention in an effective amount can be used to treat tumors. Some examples of tumors which can be treated by this method are leukemia, lung cancer, colon cancer, CNS cancer, melanoma, ovarian cancer, cervical cancer, renal cancer, prostate cancer, and breast cancer. The use of such a proactive antitumor compound or composition for the manufacture of a medicament for treating the above-mentioned tumors is also within the scope of this invention. Still another aspect of this invention is a method of treating tumor by administering to a patient such a composition. An effective amount of a proactive compound or a salt thereof is defined as the amount of the compound which, upon administration to a patient in need, confers a therapeutic effect on the treated patient. The effective amount to be administered to a patient is typically based on age, surface area, weight, and condition of the patient. The interrelationship of dosages for animals and humans (based on milligrams per meter squared of body surface) is described by Freireich et al., Cancer Chemother. Rep. 1966, 50, 219. Body surface area may be approximately determined from height and weight of the patient. See, e.g., Scientific Tables, Geigy Pharmaceuticals, Ardley, New York, 1970, 537. An effective amount of a proactive compound can range from about 0.1 mg/kg to about 250 mg/kg. Effective doses will also vary, as recognized by those skilled in the art, dependant on route of administration, excipient usage, and the possibility of co-usage with other therapeutic treatments including use of other antitumor agents and radiation therapy.

The pharmaceutical composition may be administered via the parenteral route, including orally, topically, subcutaneously, intraperitoneally, intramuscularly, and intravenously. Examples of parenteral dosage forms include aqueous solutions of the active agent, in a isotonic saline, 5% glucose or other well-known pharmaceutically acceptable excipient. Solubilizing agents such as cyclodextrins, or other solubilizing agents well-known to those familiar with the art, can be utilized as pharmaceutical excipients for delivery of the therapeutic compounds.

The proactive compound of this invention can also be formulated into dosage forms for other routes of administration utilizing conventional methods. A pharmaceutical composition can be formulated, for example, in dosage forms for oral administration in a capsule, a gel seal or a tablet. Capsules may comprise any standard pharmaceutically acceptable material such as gelatin or a cellulose derivative. Tablets may be formulated in accordance with the conventional procedure by compressing mixtures of the proactive compounds of the present invention and a solid carrier, and a lubricant. Examples of solid carriers include starch and sugar bentonite. The proactive compound can also be administered in a form of a hard shell tablet or capsule containing, for example, lactose or mannitol as a binder and a conventional filler and a tableting agent.

One way to evaluate the in vitro cytotoxic activities of a proactive compound is by incubating the tested compound with cancerous cells in serum at 37° C. for a certain period of time. After incubation, the cells can be washed and pulsed with [$^3$H] leucine in leucine-free medium for another period of time. The radioactivity of trichloroacetic acid-precipitated protein, an indication of the level of protein synthesis of the cell, can then be measured.

The antitumor activity of a proactive compound of this invention can also be preliminarily evaluated by using a tumor growth regression assay which assesses the ability of tested compounds to inhibit the growth of established solid tumors in mice. The assay can be performed by implanting tumor cells into the fat pads of nude mice. Tumor cells are then allowed to grow to a certain size before the proactive compound is administered. The volumes of tumor are then monitored for a set number of weeks, e.g., three weeks. General health of the tested animals are also monitored during the course of the assay. The results of these in vivo tests can then be compared to those obtained by administering an active, antitumor compound.

The following specific examples, which describe syntheses and biological testings of proactive compounds, are to be construed as merely illustrative, and not limitative of the remainder of the disclosure in any way whatsoever.

In the following examples, melting points were obtained on an electrothermal apparatus and are uncorrected. $^1$H and $^{13}$C nuclear magnetic resonance spectra were recorded either on a JEOL JNM-EX400 spectrometer at the National Taiwan University or on a Bruker Model AM 300 spectrometer at the National Defense Medical Center, Taipei, and reported in parts per million with DMSO-$d_6$ as internal standard on a δ scale. EI mass spectra were recorded on a JEOL JMS-D100 mass spectrometer at the National Taiwan University. Elemental analysis for C, H, and N were carried out either on a Heraeus elemental analyzer at the Cheng-Kong University, Tainan, Taiwan, or on a Perkin-Elmer 240 elemental analyzer in the National Taiwan University, and were within 0.4% of the theoretical values.

EXAMPLE 1

The following example describes the preparation of compound 22, a proactive antitumor compound of this invention. The structure of compounds 22 and those of compounds 1, 4, 5, 6, 7, 8, 9, 15, 16, 17, 18, 19, 20, and 21 are shown in Schemes 1–4, supra.

Synthesis of Compound 4

Glucuronic acid γ-lactone (88 g, 0.5 mmol) was added to 500 ml of methanol which contained 0.75 g of sodium methoxide. The mixture was stirred at room temperature for 30 minutes and at the end of which time all glucuronolactone had dissolved. After another 30 minutes, the methanol was removed under reduced pressure. The resultant syrupy solid was dissolved in 340 ml of acetic anhydride, and a mixture of 1.5 ml of perchloric acid in 10 ml of acetic anhydride was added dropwise such that reaction temperature never exceeded 40° C. The reaction mixture was stirred 24 hours at room temperature and the solution stored overnight at 4° C. to yield 64.7 g (34.4%) of crystalline material. The mother liquor was poured onto 1 kg of crushed ice and neutralized with sodium bicarbonate. Excess sodium bicarbonate was removed by filtration and the filtrate was extracted with chloroform. The chloroform extract was dried with anhydrous sodium sulfate and concentrated to a syrup. Storage at 4° C. produced an additional 52 g of crude crystalline material, resulting in an overall yield of 62%. The crystals were recrystallized once from hot methanol. $^1$H NMR (300 MHz, DMSO-$d_6$) $\delta$1.97 (s, 3H, $CH_3$), 2.00–2.01 (m, 6H, $CH_3$), 2.08 (s, 3H, $CH_3$), 3.63 (s, 3H, $OCH_3$), 4.68 (d, J=9.8 Hz, 1H, sugar-H), 4.94–5.04 (m, 2H, sugar-H), 5.52 (t, J=9.5 Hz, 1H, sugar-H), 6.02 (d, J=8.1 Hz, 1H, sugar-H); 13C NMR (75 MHz, DMSO-$d_6$) $\delta$20.5, 20.6, 20.7, 20.8, 53.0, 69.1, 70.1, 71.2, 71.7, 90.9, 167.3, 169.1, 169.4, 169.7, 169.8.

Synthesis of Compound 8

A solution of 1 g (1.33 mmol) methyl 1,2,3,4-tetra-O-acetyl-$\beta$-D-glucopyranuronate and 1.17 g (3.19 mmol) of titanium tetrabromide in 25 ml of dichloromethane was stirred at room temperature for 24 hours. The mixture was washed with ice-water and sodium bicarbonate solution, dried with sodium sulfate, and evaporated to dryness to give 0.82 g of solid. The solid was dissolved in 100 ml of acetonitrile and 275 mg (2.55 mmol) of p-hydroxybenzaldehyde and 712 mg (3.07 mmol) of silver oxide were added at room temperature for 2 hours. The material was separated by column chromatography on silica gel (ethyl acetate-hexane, 2:3) to give 528 mg of methyl 1-(4-formylphenyl)-2,3,4-tri-O-acetyl-$\beta$-D-glucopyranuronatein in a yield of 42%. $^1$H NMR (300 MHz, DMSO-$d_6$) $\delta$2.02 (s, 12H, $CH_3$), 3.63, (s, 3H, $CH_3$), 4.76 (d, J=9.9 Hz, 1H, sugar-H), 5.05–5.18 (m, 2H, sugar-H), 5.48 (t, J=9.6 Hz, 1H, sugar-H), 5.85 (d, J=7.7 Hz, 1H, sugar-H), 7.19 (d, J=7.4 Hz, 2H, ArH), 7.91 (d, J=7.4 Hz, 2H, ArH), 9.91 (s, 1H, COH); $^{13}$C NMR (75 MHz, DMSO-$d_6$) $\delta$20.6, 20.7, 53.0, 69.2, 70.7, 71.3, 71.4, 96.5, 116.8, 131.9, 132.2, 161.0, 167.3, 169.4, 169.7, 169.9, 191.9

Synthesis of Compound 9

A solution of methyl 1-(4-formylphenyl)-2,3,4-tri-O-acetyl-$\beta$-D-glucopyranuronate (528 mg, 1.2 mmol) in 100 ml of isopropanol/chloroform (1:5) was stirred with sodium borohydride (123 mg, 2.76 mmol) and silica gel (5 g) at 0° C. for 1 hour. The reaction was quenched with water and filtered to remove silica gel. The organic layer was dried with anhydrous sodium sulfate, and evaporated under reduced pressure to give a residue. The residue was washed with ethanol to produce 475 mg of methyl 1-(4-hydroxymethylphenyl)-2,3, 4-tri-O-acetyl-$\beta$-D-glucopyronuronate in a yield of 90%. $^1$H NMR (300 MHz, DMSO-$d_6$) $\delta$1.99–2.02 (m, 9H, $CH_3$), 3.63 (s, 3H, $OCH_3$), 4.43 (d, J=5.7 Hz, 2H, $CH_2$), 4.69 (d, J=10 Hz, 1H, sugar-H), 5.02–5.16 (m, 3H, sugar-H & OH), 5.47 (t, J=9.6 Hz, 1H, sugar-H), 5.62 (d, J=8.0 Hz, 1H, sugar-H), 6.94 (d, J=8.3 Hz, 2H, ArH), 7.26 (d, J=8.5 Hz, 2H, ArH); $^{13}$C NMR (75 MHz, DMSO-$d_6$) $\delta$20.6, 20.7, 20.8, 53.0, 62.7, 69.4, 70.9, 71.3, 71.4, 97.6, 106.6, 116.5, 128.3, 137.0, 155.5, 167.5, 169.4, 169.7, 169.9.

Synthesis of Compound 12

Methyl 1-(4-hydroxymethylphenyl)-2,3,4-tri-O-acetyl-$\beta$-D-glucopyronuronate (1.37 g, 3.11 mmol) was dissolved in 100 ml anhydrous methanol. 168 mg (3.11 mmol) of sodium methoxide was added at 0° C. for 30 minutes and stirred at room temperature for 2 hours. The mixture was quenched with water, extracted with dichloromethane and purified by column chromatography on silica gel (ethyl acetate) to give 590 mg of methyl 1-(4-hydroxymethylphenyl)-$\beta$-D-glucopyranuronatein in 60.2% yield. MS m/z, 314.255 (FAB$^+$); $^1$H NMR (200 MHz, DMSO-$d_6$) $\delta$3.22–3.42 (m, 3H, sugar-H), 3.61 (s, 3H, $OCH_3$), 4.09 (d, J=8.6 HZ, 1H, sugar-H), 4.37 (d, J=5.2 Hz, 2H, $CH_2$), 5.0 (d, J=7.1 Hz, 1H, sugar-H), 5.04 (s, 1H, OH), 5.24 (s, 1H, OH), 5.38–5.43 (m, 2H, OH), 6.92 (d, J=8.0 Hz, 2H, ArH), 7.19 (d, J=8.0 Hz, 2H, ArH); $^{13}$C NMR (50 MHz, DMSO-$d_6$) $\delta$53.0, 63.0, 72.3, 73.9, 76.0, 76.5, 101.2, 117, 129, 137, 156.4, 170.2.

Synthesis of Compound 15

Compound 1 (200 mg, 0.55 mmol) was dissolved in 1.5 ml of cold sulfuric acid (sp. gr. 1.84) in a 100 ml round-bottomed flask immersed in an ice-salt bath. The mixture was cooled to about 4° C., and 1.1 ml of fuming nitric acid (sp. gr. 1.50) was added dropwise such that the reaction temperature never exceeded 20° C. The mixture was stirred in an ice-salt bath for 10 minutes before the solution was poured onto 250 mg of crushed ice and neutralized with sodium bicarbonate. The yellow solid was collected by filtration, and the filtrate was extracted with chloroform to give 208 mg of compound 15 in 92.6% yield. $^1$H NMR (400 MHz, DMSO-$d_6$) $\delta$0.88 (t, 3H, $CH_3$), 1.85 (m, 2H, $CH_2$), 5.24 (s, 2H, $CH_2$), 5.40 (s, 2H, $CH_2$), 6.50 (s, 1H, OH), 7.28 (s, 1H, ArH), 7.63 (d, J=9.3 Hz, 2H, ArH), 8.24 (d, J=5.8 Hz, 1H, ArH), 8.41 (s, 1H, ArH).

Synthesis of Compound 16

A solution of compound 15 (200 mg, 0.49 mmol) in dichloromethane (10 ml) was stirred with triethylamine (1 drop) and N,N-dimethylaminopyridine (66 mg, 0.54 mmol) at room temperature for 5 min. 103 mg (0.54 mmol) of p-toluenesulfonyl chloride was then stirred with the reaction mixture at room temperature for 30 minutes. The reaction was quenched with water, neutralized with 1N hydrochloric acid, extracted with chloroform, dried with anhydrous sodium sulfate, and concentrated to a residue. The residue was purified by column chromatography on silica gel (chloroform) to give 260 mg of compound 16 in 95% yield. $^1$H NMR (400 MHz, DMSO-$d_6$) $\delta$0.86 (t, J=7.3 Hz, 3H, $CH_3$), 1.87–1.94 (m, 2H, $CH_2$), 2.44 (s, 3H, $CH_3$), 5.27 (s, 2H, $CH_2$), 5.42 (s, 2H, $CH_2$), 6.56 (s, 1H, OH), 7.38 (s, 1H, ArH), 7.52 (d, J=8.2 Hz, 2H, ArH), 7.85–7.79 (m, 3H, ArH), 8.50 (d, J=9.3Hz, 1H, ArH), 8.59 (s, 1H, ArH).

Synthesis of Compound 17

A solution of compound 16 (1.45 g, 2.57 mmol) in dioxane (80 ml) was mixed with palladium acetate (144 mg, 0.64 mmol) and triphenylphosphine (674 mg, 2.57 mmol) at room temperature under argon atmosphere. The temperature was raised to 90° C. and 30 ml of 1M triethylammonium formate in dioxane was added dropwise over a period of 1.5 h. The reaction mixture was cooled to room temperature, diluted with chloroform, and washed with water. The crude product was purified by column chromatography on silica gel (methanol-chloroform, 5:95) to give 884 mg of compound 17 in 94.5% yield. $^1$H NMR (300 MHz, DMSO-$d_6$) $\delta$0.88 (t, J=7.1 Hz, 3H, $CH_3$), 1.85 (m, 2H, $CH_2$), 5.28 (s, 2H, $CH_2$), 5.43 (s, 2H, $CH_2$), 6.13 (s, 2H, $NH_2$), 6.52 (s, 1H, OH), 6.81 (d, J=9.0 Hz, 1H, ArH), 7.30 (s, 1H, ArH), 7.34 (d, J=8.4 Hz, 1H, ArH), 7.53 (t, J=9.0 Hz, 1H, ArH), 8.85 (s, 1H, ArH); $^{13}$C NMR (75 MHz, DMSO-$d_6$) $\delta$8.2, 30.7, 50.6, 65.6, 72.8, 96.8, 108.9, 116.6, 117.9, 119.0, 126.9, 127.5, 131.6, 146.1, 149.6, 150.4, 152.2, 157.3, 163.3, 172.9.

Synthesis of Compound 18

A solution of compound 17 (200 mg, 0.55 mmol) in 100 ml of acetonitrile/benzene (1:1) was stirred at 60° C. while a solution of triphosgene (160 mg, 0.54 mmol) in toluene (5 ml) was added. The mixture was stirred at 80° C. for 1 hour before addition of methyl 1-(4-hydroxymethylphenyl)-$\beta$-D-glucopyranuronate (350 mg, 1.16 mmol). After stirring at 80° C. for an addition hour, the mixture was cooled to room temperature, quenched with water, and extracted with chloroform. The crude product was purified by column chromatography on silica gel (methanol-chloroform, 1:9) to give 125 mg of compound 18 in 32.3% yield. LC-MS: m/z, 353 (M$^+$+1), M=704/2=352; $^1$H NMR (200 MHz, DMSO-$d_6$) $\delta$0.86 (t, J=7.0 Hz, 3H, $CH_3$), 1.86 (m, 2H, $CH_2$), 3.23–3.50

(m, 3H, sugar-H), 3.66 (s, 3H, OCH$_3$), 4.08 (d, J=8.6 Hz, 1H, sugar-H), 5.16 (s, 2H, CH$_2$), 5.30 (s, 2H, CH$_2$), 5.45–5.52 (m, 3H, CH$_2$ & sugar-H), 6.56 (s, 1H, OH), 7.06 (d, J=8.4 Hz, 2H, ArH), 7.36 (s, 1H, ArH), 7.43 (d, J=8.2 Hz, 2H, ArH), 7.81 (m, 1H, ArH), 8.00 (m, 1H, ArH), 8.83 (s, 1H, ArH), 9.93 (s, 1H, ArH), 11.14 (br s, 1H, OH).

Synthesis of Compound 22

Compound 18 (125 mg, 0.18 mmol) was mixed with potassium trimethylsilanolate (60 mg, 0.45 mmol) in anhydrous tetrahydrofuran (25 ml) at ambient temperature under nitrogen for 2 hours. The yellow solid was filtered under nitrogen, dissolved in water, and washed with chloroform. The water layer was acidified with 1N hydrochloric acid, then stand in ice bath, compound 22 was precipitated, collected the crude by filter. The crude was purified by reverse phase column chromatography on silica gel (20% acetonitrile-water) gave 60 mg of purified compound 22 in 505 yield. LC-MS, m/z, 690.3 (M$^+$, lactone form), 706.3 (M$^+$, carboxylate form); $^1$H NMR (200 MHz, CD$_3$CN+D$_2$O) δ0.89 (t, J=7.2 Hz, 3H, CH$_3$), 1.86–1.90 (m, 2H, CH$_2$), 3.45–3.47 (m, 3H, sugar-H), 3.84–3.90 (m, 3H, CH$_2$ & sugar-H), 4.98 (d, J=6.7 Hz, 1H, sugar-H), 5.11 (2, 2H, CH$_2$), 5.15 (s, 2H, CH$_2$), 7.05 (d,J=8.4 Hz, 2H, ArH), 7.34 (d,J=8.4 Hz, 2H, ArH), 7.49 (s, 1H, ArH), 7.71–7.75 (m, 2H, ArH), 7.94 (d, J=7.7 Hz, 1H, ArH), 8.59 (s, 1H, ArH); Elemental analysis: calculated for C$_{34}$H$_{31}$N$_3$O$_{13}$+5.5 H$_2$O (788.7148):C, 51.78; H, 5.36; N, 5.32, found: C, 51.96; H, 5.07; N, 5,27.

20 μl samples made from compounds 22 and 17 (moiety (3) of compound 22) were injected onto a Hypersil column (RP-18, 4.6×250 mm, 5 μm) with 45% methanol and 25 mM phosphate buffer (pH 2.5) as mobile phase at a flow rate of 1 ml/min. Eluted components were detected by fluorescence (excitation: 397 nM, emission: 482 nM) on a Gilson fluorometer. Peak areas were analyzed with Beckman system Gold software. The retention times for compound 17 and compound 22 were 9.5 and 15.8 minutes, respectively.

A proactive antitumor compound by which moieties (2) and (3) are linked together via a carbonate linkage was also prepared. Such compounds are not within the scope of this invention.

Compound 12, methyl 1-(4-hydroxymethylphenyl)-β-D-glucuronate (0.21 g, 0.67 mmol), was dissolved in acetonitrile (30 ml) which contained 5 drops of pyridine before 4-nitrophenyl chloroformate (135 mg, 0.67 mmol) was added and stirred for 1 hour. Solvent was removed under reduced pressure. The residue was purified by column chromatography on silica gel (ethyl acetate) to give 125 mg of methyl 1-[4-(4-nitrophenyl)benzyloxy carbonyl]-β-D-glucopyranuronate (compound 13) in 41% yield. $^1$H NMR (200 MHz, DMSO-d$_6$) δ3.36–3.37 (m, 3H, sugar-H), 3.67 (s, 3H, OCH3), 4.10 (d, J=8.6 Hz, 1H, sugar-H), 5.16 (d, J=6.9 Hz, 1H, sugar-H), 5.20–5.30 (m, 2H, CH2 & OH), 5.45–5.51 (m, 2H, OH), 7.05 (d, J=8.3 Hz, 2H, ArH), 7.44 (d, J=8.3 Hz, 2H, ArH), 7.59 (d, J=9.0 Hz, 2H, ArH), 8.33 (d, J=9.0 Hz, 2H, ArH).

Compound 1 (150 mg, 0.41 mmol) and triethylamine (1 drop) in dimethylformide (10 ml) was stirred with compound 13 (236 mg, 0.49 mmol) at room temperature for 6 hours. Solvent was removed under reduced pressure. The residue was purified by column chromatography on silica gel (methanol-chloroform, 5:95) to give 68 mg of compound 14 in 24% yield. Compound 14 is similar to compound 18 except that the carbamate linkage is replaced with a carbonate linkage. $^1$H NMR (200 MHz, DMSO-d$_6$) δ0.87 (t, J=7.3 Hz, 3H, CH$_3$), 1.0–1.25 (m, 2H, CH$_2$), 3.30–3.45 (m, 3H, sugar-H), 3.65 (s, 3H, OCH$_3$), 4.08 (d, J=8.8 Hz, 1H, sugar-H), 5.13 (d, J=7 Hz, 1H, sugar-H), 5.41 (s, 2H, CH$_2$), 5.10–5.40 (m, 3H, OH), 6.54 (s, 1H, OH), 7.06 (d, J=8.4 Hz, 2H, ArH), 7.34 (s, 1H, ArH), 7.43 (d, J=8.4 Hz, 2H, ArH), 7.78 (dd, J=9.2 Hz, J=2.3 Hz, 1H, ArH), 8.03 (d, J=2.3 Hz, 1H, ArH), 8.21 (d, J=9.2 Hz, 1H, ArH), 8.67 (s, 1H, ArH).

Hydrolysis of compound 14 yielded compound 23, a compound identical to compound 22, except that it has a carbonate linkage instead of a carbamate linkage.

EXAMPLE 2

The following example describes the preparation of a proactive antitumor compound having the formula of claim 1 in which Z is H; each of R$^2$, R$^3$, and R$^4$ is OH; X is benzene; R$^b$ is NO$_2$ (ortho to the ether linkage); R$^5$ are H; n is 0; and m is 1.

Synthesis of Compound 5

0.5 g (1.33 mmol) of methyl 1,2,3,4-tetra-O-acetyl-β-D-glucopyranuronate (prepared as described in Example 1) and 0.5 g (1.36 mmol) of titanium tetrabromide were dissolved in 15 ml of dichloromethane and stirred at room temperature for 18 hours. The mixture was washed with ice-water and sodium bicarbonate solution, dried with sodium sulfate, and evaporated to dryness to give 0.6 g of syrupy solid. The syrupy solid was dissolved in 50 ml of acetonitrile, and 156 mg (1.02 mmol) of 2-nitro-4-methylphenol and 355 mg (1.53 mmol) of silver oxide were added at room temperature for 2 hours. The material was separated by column chromatography on silica gel (ethyl acetate-hexane, 3:7) to give 346 mg of methyl 1-(2-nitro-4-methylphenyl)-2,3,4-tri-O-acetyl-β-D-glucopyranuronate in 55.5% yield. $^1$H NMR (300 MHz, DMSO-d$_6$) δ 2.0 (s, 3H, CH$_3$), 2.02 (s, 6H, CH$_3$), 2.33 (s, 3H, ArCH$_3$), 3.65 (s, 3H, OCH$_3$), 4.73 (dd, J=9.8 Hz, J=1.9 Hz, 1H, sugar-H), 5.10 (m, 2H, sugar-H), 5.45 (m, 1H, sugar-H), 5.68 (m, 1H, sugar-H), 7.30 (dd, J=8.6 Hz, J=1.7 Hz, 1H, ArH), 7.51 (d, J=8.6 Hz, 1H, ArH), 7.72 (s, 1H, ArH); $^{13}$C NMR (75 MHz, DMSO-d$_6$) δ20.1, 20.6, 20.7, 39.0, 53.0, 69.1, 70.3, 71.1, 71.3, 98.5, 118.2, 125.0, 133.9, 135.0, 140.6, 146.4, 167.3, 169.1, 169.7, 169.9.

Synthesis of Compound 6

N-bromosuccinimide (117.2 mg, 0.66 mmol) and benzoyl peroxide (159 mg, 0.66 mmol) were added to a solution of methyl 1-(2-nitro-4-methylphenyl)-2,3,4-tri-O-acetyl-β-D-glucopyranuronate (206 mg, 0.44 mmol) in carbon tetrachloride (20 ml). The mixture was refluxed for 5 hours and stirred at room temperature for 12 hours. The reaction mixture was evaporated under reduced pressure, and purified by column chromatography on silica gel (ethyl acetate-hexane, 2:3) to give 47 mg of methyl 1-(2-nitro-4-bromomethylene-phenyl)-2,3,4-tri-O-acetyl-β-D-glucopyranuronate in 20% yield. $^1$H NMR (300 MHz, DMSO-d$_6$) δ1.98–2.02 (m, 9H, CH$_3$), 3.64 (s, 3H, OCH$_3$), 4.73 (s, 2H, CH$_2$), 4.77 (s, 1H, sugar-H), 5.09–5.13 (m, 2H, sugar-H), 5.47 (t, J=9 Hz, 1H, sugar-H), 5.76 (d, J=7.7 Hz, 1H, sugar-H), 7.43 (d, J=8.7 Hz, 1H, ArH), 7.76 (d, J=8.7 Hz, 1H, ArH), 8.02 (s, 1H, ArH).

Synthesis of Compound 7

A solution of methyl 1-(2-nitro-4-formylphenyl)-2,3,4-tri-O-acetyl-β-D-glucopyranuronate (2.39 g, 4.94 mmol) in 200 ml of isopropanol/chloroform (1:5) was stirred with sodium borohydride (374 mg, 9.89 mmol) and silica gel (8 g) at 0° C. for 30 minutes. The reaction was quenched in water and filtered to remove silica gel. The organic layer was dried with sodium sulfate, and evaporated under reduced pressure to give a residue. The residue was washed with ethanol to obtain 1.78 g of methyl 1-(2-nitro-4-hydroxymethylphenyl-2,3, 4-tri-O-acetyl-β-D-glucopyranuronate in a yield of 74.2%. $^1$H NMR (300 MHz, DMSO-d$_6$) δ2.0 (m, 9H, CH$_3$), 3.64 (s, 3H, OCH$_3$), 4.51 (d, J=5.5 Hz, 2H, CH$_2$), 4.73 (d, J=9.3 Hz, 1H, sugar-H), 5.05–5.14 (m, 2H, sugar-H), 5.41–5.49 (m, 2H, sugar-H & OH), 5.71 (d, J=7.7 Hz, 1H, sugar-H), 7.38 (d, J=8.2 Hz, 1H, ArH), 7.62 (d, J=8.8 Hz, 1H, ArH), 7.80 (s, 1H, ArH); $^{13}$C NMR (75 MHz, DMSO-d$_6$) δ20.6, 20.7, 20.8, 53.0, 61.7, 69.1, 70.3, 71.1, 71.4, 98.4, 118.1, 122.7, 132.4, 138.9, 140.5, 167.3, 169.1, 169.7, 169.9; Elemental analysis: calculated for $C_{20}H_{23}O_{13}N$ (485.4609): C, 49.48; H, 4.78, N, 2.90, found: C, 49.28, H, 4.85, N, 2.98.

Compound 7 can then be hydrolyzed in a fashion analogous to that in which compound 9 was hydrolyzed (see Example 1). The hydrolyzed compound can be subsequently coupled to compound 19 to produce a proactive antitumor compound.

EXAMPLE 3

500 μl of compound 22 (116 μM) in βG buffer (100 mM acetic acid, 50 mM bis-tris, 50 mM triethanolamine, pH 7.0) was incubated with *E. coli* β-glucuronidase (1 μg/ml) at 37° C. Aliquots (30 μl) withdrawn after 0, 1, 2, 3, and 5 minutes was mixed with 300 μl of ethyl acetate, and acidified by addition of 12 mM phosphoric acid (270 μl). The samples were extracted three times with ethyl acetate, and dried in a speed-vacuum. The recovery of compounds 22 and 17 from βG buffer (pH 7.2) were about 90% and 80%, respectively. Samples were suspended in 150 μl of mobile phase (45% methanol/25 mM phosphate buffer, pH 2.5) and analyzed by HPLC. The results showed that the absorbance of compound 22 is almost undetectable after 3 minutes, and the absorbance of compound 17 increased in the first three minutes and reached a steady level after the third minute. This result thus demonstrated that compound 22 was converted into its moiety (3), i.e., compound 17, upon activation by glucuronidase.

In another experiment, compound 22 (145 μM, 100 μg/ml) was incubated in 95% human plasma at 37° C. in an atmosphere of $CO_2$. Aliquots (30 μl) withdrawn after 0, 1, 3, 5, 12, 22, 30.5 and 48 hours were mixed with 600 μl of ethyl acetate to precipitate protein, and acidified with 12 mM phosphoric acid (570 μl). Samples were extracted three times with ethyl acetate, and dried in a speed-vacuum. The recoveries of compounds 22 and 17 in 95% human plasma were approximately 80% and 90%, respectively. The result shows that compound 22 had a surprisingly long half life in serum, as compared with compound 23. Compound 23 demonstrated a half life of only 90 minutes in 10% bovine serum at 37° C.

EXAMPLE 4

CaSki human cervical carcinoma cells were plated overnight in 96-well microtiter plates at 18,000 cells/well. Serial dilution of (i) compound 17 alone, (ii) compound 22 with β-glucuronidase, and (iii) compound 22 alone, in medium containing 5% fetal calf serum were added to cells for 96 hours at 37° C. Cells were subsequently washed once with sterile PBS, and then pulsed for 2 hours with [$^3$H] leucine (1 μCi/well) in leucine-free medium. The radioactivity of trichloroacetic acid-precipitated protein was measured in a Beckman LS 6000 series liquid scintillation counter. In both tests (i) and (ii), the level of protein synthesis of the cancerous cells (as seen from the level of radioactivity) was affected by the presence of the cytotoxic agent and decreased by almost 4-fold at a low concentration of 100 nM. In comparison, the level of protein synthesis of the cancerous cells in test (iii) did not change at 100 nM, thus showing that compound 22 is much less cytotoxic than compound 17, but will become almost as cytotoxic as compound 17 upon activation by glucuronidase.

Other Embodiments

From the above description, one skilled in the art can easily ascertain the essential characteristics of the present invention, and without departing from the spirit and scope thereof, can make various changes and modifications of the invention to adapt it to various usages and conditions. For example, enzyme-substrate pair other than glucuronidase-glucuronide, although not described above, can also function as a part of the proactive compound-enzyme system. As another example, also within the scope of this invention is a proactive antitumor compound with its antitumor moiety slightly different from moiety (3) as described above. Thus, other embodiments are also within the claims.

What is claimed is:

1. A proactive antitumor compound of the following formula:

[Chemical structure]

wherein
  $R^1$ is COOZ; Z being H or $K^+$;
  each of $R^2$, $R^3$, and $R^4$, independently, is OH;
  X is benzene or pyridine, optionally substituted with $R^b$;
    $R^b$ being H, $C_{1-5}$ alkyl, $C_{1-5}$ alkoxy, $NO_2$, F, Cl, Br, $SO_3H$, and CN;
  $R^5$ is H or OH; and
  each of n and m, independently, is 0 or 1;
  or a salt thereof.

2. The proactive antitumor compound of claim 1, wherein Z is H; or a salt thereof.

3. The proactive antitumor compound of claim 2, wherein X is benzene; and $R^b$ is H or $NO_2$; or a salt thereof.

4. The proactive antitumor compound of claim 3, wherein $R^b$ is at an ortho position with respect to the ether linkage; or a salt thereof.

5. The proactive antitumor compound of claim 4, wherein $R^b$ is H; n is 0; and m is 1; or a salt thereof.

6. The proactive antitumor compound of claim 5, wherein $R^5$ is H; or a salt thereof.

7. The proactive antitumor compound of claim 1, wherein X is benzene; and $R^b$ is H or $NO_2$; or a salt thereof.

8. The proactive antitumor compound of claim 7, wherein $R^b$ is at an ortho position with respect to the ether linkage; or a salt thereof.

9. The proactive antitumor compound of claim 8, wherein $R^b$ is H; n is 0; and m is 1; or a salt thereof.

10. The proactive antitumor compound of claim 9, wherein $R^5$ is at an ortho position with respect to the carbamate linkage; or a salt thereof.

11. The proactive antitumor compound of claim 9, wherein $R^5$ is H; or a salt thereof.

12. The proactive antitumor compound of claim 1, wherein $R^5$ is at an ortho position with respect to the carbamate linkage; or a salt thereof.

13. The proactive antitumor compound of claim 1, wherein $R^5$ is H; or a salt thereof.

14. The proactive antitumor compound of claim 12, wherein Z is H or $K^+$; and each of $R^2$, $R^3$, and $R^4$ is OH; or a salt thereof.

15. The proactive antitumor compound of claim 14, wherein Z is H; or a salt thereof.

16. The proactive antitumor compound of claim 13, wherein Z is H or $K^+$; and each of $R^2$, $R^3$, and $R^4$ is OH; or a salt thereof.

17. The proactive antitumor compound of claim 16, wherein Z is H; or a salt thereof.

18. The proactive antitumor compound of claim 1, wherein n is 0.

19. The proactive antitumor compound of claim 18, wherein m is 1.

* * * * *